United States Patent
Smits et al.

(10) Patent No.: US 11,254,643 B2
(45) Date of Patent: Feb. 22, 2022

(54) PROCESS FOR PRODUCING HERBICIDAL PYRIDAZINONE COMPOUNDS

(71) Applicant: Syngenta Participations AG, Basel (CH)

(72) Inventors: Helmars Smits, Münchwilen (CH); Denis Gribkov, Münchwilen (CH); Edouard Godineau, Stein (CH); Christopher Charles Scarborough, Stein (CH); Alan James Robinson, Münchwilen (CH); Michael Christian Dieckmann, Münchwilen (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/757,303

(22) PCT Filed: Oct. 16, 2018

(86) PCT No.: PCT/EP2018/078296
§ 371 (c)(1),
(2) Date: Apr. 17, 2020

(87) PCT Pub. No.: WO2019/076930
PCT Pub. Date: Apr. 25, 2019

(65) Prior Publication Data
US 2021/0024470 A1 Jan. 28, 2021

(30) Foreign Application Priority Data
Oct. 18, 2017 (GB) ..................................... 1717080

(51) Int. Cl.
*C07D 403/12* (2006.01)
*C07D 237/14* (2006.01)

(52) U.S. Cl.
CPC .................. *C07D 237/14* (2013.01)

(58) Field of Classification Search
CPC .. C07D 403/12; C07D 237/14; A61K 31/501; A61K 31/50
USPC ..................... 544/238, 239; 514/247, 252.01
See application file for complete search history.

(56) References Cited

U.S. PATENT DOCUMENTS

| | | | |
|---|---|---|---|
| 10,813,354 B2 * | 10/2020 | Burton | A01N 43/58 |
| 2005/0020594 A1 | 1/2005 | Hepperle et al. | |

FOREIGN PATENT DOCUMENTS

| | | |
|---|---|---|
| DE | 4423934 A1 | 3/1995 |
| EP | 1070055 A1 | 1/2001 |
| EP | 1470112 | 10/2004 |
| EP | 2518063 A1 | 10/2012 |
| EP | 2694483 A1 | 2/2014 |
| GB | 600532 A1 | 4/1948 |
| WO | 99/52878 A1 | 10/1999 |
| WO | 2005007632 A1 | 1/2005 |
| WO | 2012136703 A1 | 10/2012 |
| WO | 2017178582 A1 | 10/2017 |

OTHER PUBLICATIONS

Gregory et al., Journal of the Chemical Society dated Jan. 1, 1949.
Stevens et al., Journal of the American Chemical Society dated Jan. 1, 1955.
Overend et al., Juournal of the Chemical Society dated Jan. 1, 1947.
Overend et al., The Conversion of Sucrose into Pyridazine Derivatives dated Jan. 1, 1950.
International Search Report and Written Opinion for International Application No. PCT/EP2018/078296, dated Dec. 17, 2018.

* cited by examiner

*Primary Examiner* — Jeffrey H Murray
(74) *Attorney, Agent, or Firm* — BakerHostetler; Toni-Junell Herbert

(57) ABSTRACT

The present invention provides, inter alia, a process for producing a compound of Formula (I): wherein $A^1$, $R^1$, $R^2$, $R^3$, $R^4$, $R^5$ and $R^6$ are as defined herein. The present invention further provides intermediate compounds utilised in said process, and methods for producing said intermediate compounds.

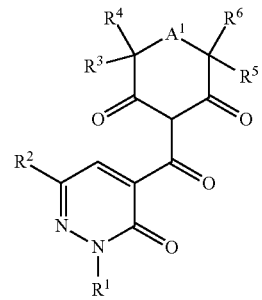

15 Claims, No Drawings

PROCESS FOR PRODUCING HERBICIDAL PYRIDAZINONE COMPOUNDS

CROSS-REFERENCE TO RELATED APPLICATIONS

This application is a 371 National Stage application of International Application No. PCT/EP2018/078296 filed Oct. 16, 2018 which claims priority to GB 1717080.4, filed Oct. 18, 2017, the entire contents of which applications are hereby incorporated by reference.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS WEB)

Not Applicable.

STATEMENT REGARDING PRIOR DISCLOSURE BY THE INVENTOR OR A JOINT INVENTOR

Not Applicable.

BACKGROUND

The present invention relates to a process for producing herbicidal pyridazinone compounds. Such compounds are known, for example, from WO 2012/136703 and WO2017/178582. As explained therein, such compounds are typically produced by forming an acid chloride of the corresponding pyridazinone acid and coupling it with the cyclohexanedione in the presence of base. This reaction first produces an enol ester which can be rearranged to a compound of Formula (I) using a catalytic amount of cyanide source, for example acetone cyanohydrin. However the yields obtained are not ideal for a large scale production and the use of highly toxic cyanides on a manufacturing scale is undesirable. Therefore alternative, more efficient synthesis methods are desired.

SUMMARY

The present invention provides an alternative carbonylative arylation process which (i) avoids the need to produce the acid chloride and (ii) avoids a cyanide catalysed rearrangement. The synthesis of enol esters by reacting aryl halides with cyclohexanedione and carbon monoxide in the presence of a base and palladium catalyst has been described (Negishi, E.; Liou, S.; Xu, C.; Shimoyama, I.; Makabe, H. J. Mol. Cat. A: Chem. 1999, 143, 279). However, the reaction proceeds no further than the enol esters, which can be isolated in good yield. Surprisingly, it has now been found that when aryl group is replaced by a specific pyridazinone group, as present in a compound of Formula (II), the initial enol ester produced actually rearranges under the reaction conditions to form the compound of Formula (I) in high yields.

Thus, according to the present invention there is provided a process for producing a compound of Formula (I):

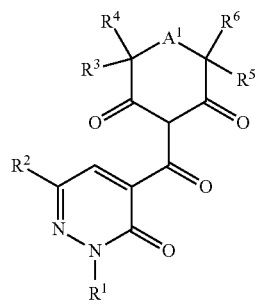

wherein
$R^1$ is selected from the group consisting of hydrogen, $C_1$-$C_6$alkyl, $C_1$-$C_6$haloalkyl, $C_1$-$C_3$alkoxy$C_1$-$C_3$alkyl-, $C_1$-$C_3$alkoxy$C_2$-$C_3$alkoxy$C_1$-$C_3$alkyl-, aryl and a 5 or 6-membered heteroaryl, wherein the heteroaryl contains one to three heteroatoms each independently selected from the group consisting of oxygen, nitrogen and sulphur, and wherein the aryl and heteroaryl component may be optionally substituted;
$R^2$ is $C_1$-$C_6$ alkyl or $C_3$-$C_6$ cycloalkyl;
$A^1$ is selected from the group consisting of O, C(O) and ($CR^7R^8$); and
$R^4$, $R^6$, $R^7$ and $R^8$ are each independently selected from the group consisting of hydrogen and $C_1$-$C_4$alkyl;
$R^3$ and $R^5$ are each independently selected from the group consisting of hydrogen and $C_1$-$C_4$alkyl or together may form a $C_1$-$C_3$alkylene chain;
the process comprising reacting a compound of Formula (II)

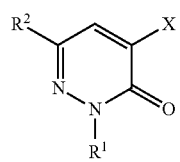

wherein X is a halogen;
with a compound of Formula (III)

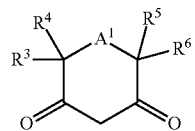

wherein $A^1$ and $R^3$, $R^4$, $R^5$ and $R^6$ are as defined with regard to Formula (I) above; in a reaction medium comprising:
(i) a palladium catalyst;
(ii) a suitable phosphine ligand or phosphine ligand salt;
(iii) a suitable base; and
(iv) carbon monoxide;
to give a compound of Formula (I).

$C_1$-$C_6$alkyl and $C_1$-$C_4$alkyl groups referred to above include, for example, methyl (Me, $CH_3$), ethyl (Et, $C_2H_5$), n-propyl (n-Pr), isopropyl (i-Pr), n-butyl (n-Bu), isobutyl (i-Bu), sec-butyl and tert-butyl (t-Bu).

Halogen (or halo) includes fluorine, chlorine, bromine and iodine.

$C_1$-$C_6$haloalkyl includes, for example, fluoromethyl-, difluoromethyl-, trifluoromethyl-, chloromethyl-, dichloromethyl-, trichloromethyl-, 2,2,2-trifluoroethyl-, 2-fluoroethyl-, 2-chloroethyl-, pentafluoroethyl-, 1,1-difluoro-2,2,2-trichloroethyl-, 2,2,3,3-tetrafluoroethyl-, 2,2,2-trichloroethyl-, heptafluoro-n-propyl and perfluoro-n-hexyl. $C_1$-$C_4$haloalkyl includes, for example, fluoromethyl-, difluoromethyl-, trifluoromethyl-, chloromethyl-, dichloromethyl-, trichloromethyl-, 2,2,2-trifluoroethyl-, 2-fluoroethyl-, 2-chloroethyl-, pentafluoroethyl-, 1,1-difluoro-2,2,2-trichloroethyl-, 2,2,3,3-tetrafluoroethyl-, 2,2,2-trichloroethyl- and heptafluoro-n-propyl-. Preferred $C_1$-$C_6$haloalkyl groups are fluoroalkyl groups, especially difluoroalkyl and trifluoroalkyl groups, for example, difluoromethyl and trifluoromethyl.

$C_3$-$C_6$ cycloalkyl groups include, for example, for example cyclopropyl, cyclobutyl, cyclopentyl or cyclohexyl.

$C_1$-$C_3$alkoxy$C_1$-$C_3$alkyl- includes, for example, methoxymethyl, methoxyethyl, ethoxymethyl, ethoxyethyl, n-propoxymethyl, n-propoxyethyl, isopropoxymethyl or isopropoxyethyl.

$C_1$-$C_3$alkoxy$C_2$-$C_3$alkoxy$C_1$-$C_3$alkyl- includes, for example, methoxyethoxymethyl-.

Nitro, as used herein, refers to the group —$NO_2$.

Aryl, as used herein, refers to an unsaturated aromatic carbocyclic group of from 6 to 10 carbon atoms having a single ring (e.g., phenyl) or multiple condensed (fused) rings, at least one of which is aromatic (e.g., indanyl, naphthyl). Preferred aryl groups include phenyl, naphthyl and the like. Most preferably, the aryl group is a phenyl group. The phenyl ring may be unsubstituted or in mono- or poly-substituted form, in which case the substituents may, as desired, be in the ortho-, meta- and/or para-position(s).

A 5 or 6-membered heteroaryl group, wherein the heteroaryl contains one to three heteroatoms each independently selected from the group consisting of oxygen, nitrogen and sulphur includes, for example, furanyl, thiophenyl, thiazolyl, oxazolyl, isoxazolyl, thiazolyl, pyrazolyl, isothiazolyl, pyridyl, pyridazinyl, pyrazinyl, pyrimidinyl and triazolyl. The heteroaryl component may be optionally mono or poly substituted as described.

Where the aryl or heteroaryl components described above are substituted, the one or more substituents are preferably selected from the group consisting of halo, $C_1$-$C_4$alkyl, $C_1$-$C_4$haloalkyl, $C_1$-$C_3$ alkoxy, cyano and nitro.

In one embodiment of the present invention, $R^1$ is an optionally substituted heteroaryl.

In another embodiment of the present invention, $R^1$ is an optionally substituted phenyl, preferably 3,4-dimethoxyphenyl.

In one embodiment of the present invention, $R^2$ is methyl.

In a particularly preferred embodiment of the present invention, $R^1$ is 3,4-dimethoxyphenyl and $R^2$ is methyl.

In a preferred embodiment of the invention, X is Br or Cl, most preferably Br.

In one embodiment of the present invention $A^1$ is $CR^7R^8$ and $R^3$, $R^4$, $R^5$, $R^6$, $R^7$ and $R^8$ are hydrogen. Thus, in a particularly preferred embodiment of the present invention the compound of Formula (III) is cyclohexanedione.

In one embodiment of the present invention, $A^1$ is $CR^7R^8$ and $R^4$, $R^6$, $R^7$ and $R^8$ are hydrogen and $R^3$ and $R^5$ together form an ethylene chain.

In a particularly preferred embodiment of the present invention, $A^1$ is $CR^7R^8$ and $R^3$, $R^4$, $R^5$, $R^6$, $R^7$ and $R^8$ are hydrogen, $R^1$ is 3,4-dimethoxyphenyl and $R^2$ is methyl.

Suitable palladium catalysts (i) include, but are not limited to $Pd(OAc)_2$, $PdCl_2$, Pd/C, $PdBr_2$, $PdCl_2(PhCN)_2$, $Pd_2dba_2$, $Pd(PPh_3)_4$ and $PdCl_2(cinnamyl)_2$. The most preferred catalyst is $Pd(OAc)_2$. The amount of palladium catalyst is between 0.0001 and 0.05 equivalents, more preferably between 0.0001 and 0.001 equivalents.

Suitable phosphine ligand or phosphine ligand salts (ii) include, but are not limited to monodentate phosphines such as $Ph_3P$, $Cy_3P$, $nBuPAd_2$, $tBu_3P \cdot HBF_4$ and XPhos as well bidentate ligands such as Xantphos, Josiphos, DPEPhos, dcpb, dcpp and BINAP. The most preferred phosphine ligands are Xantphos and DPEPhos when X=Br and dcpb when X=Cl. The amount of phosphine ligands is between 0.0001 and 0.05 equivalents, more preferably between 0.0001 and 0.001 equivalents.

Suitable bases (iii) include, but are not limited to inorganic bases such as $K_2CO_3$, $Cs_2CO_3$, $Na_2CO_3$, NaOH as well as amine bases such as triethylamine, diisopropylethylamine and DBU. The most preferred bases are triethylamine and diisopropylethylamine.

The process of the present invention is conducted in the presence of carbon monoxide, typically under an atmosphere of carbon monoxide. The pressure is from 1 to 50 bar, more preferably between 2 and 10 bar. Alternatively, the carbon monoxide can be generated during the process using a suitable carbon monoxide generator or precursor.

In a preferred embodiment of the present invention, the reaction medium further comprises a solvent (v). Suitable solvents include, but are not limited to polar aprotic solvents such as acetonitrile, anisole, dioxane, THF, EtOAc, MTBE, PrCN. The most preferred solvent is acetonitrile.

Further provided is a compound of Formula (IIa)

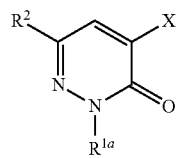

(IIa)

wherein $R^{1a}$ is an optionally substituted phenyl and $R^2$ and X are as defined above.

Further provided is a compound of Formula (IIa1)

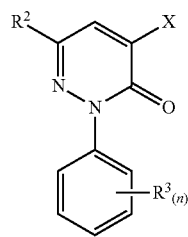

(IIa1)

wherein $R^2$ and X are as defined above, and $R^3$ is selected from the group consisting of halo, $C_1$-$C_4$alkyl, $C_1$-$C_4$haloalkyl, $C_1$-$C_3$ alkoxy-, cyano and nitro; and n=0, 1,2 or 3.

The present invention still further provides a compound of Formula (IIa), wherein $R^2$ in methyl, X is Br and $R^{1a}$ is 3,4-dimethoxyphenyl (i.e 4-Bromo-2-(3,4-dimethoxyphenyl)-6-methyl-pyridazin-3-one/a compound of Formula (IIa1a))

(IIa1a)

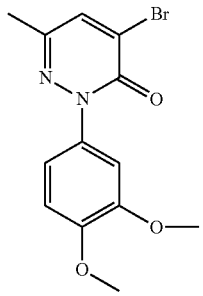

DETAILED DESCRIPTION

The following scheme describes the reactions of the invention in more detail. The substituent definitions are the same as defined above.

Scheme 1

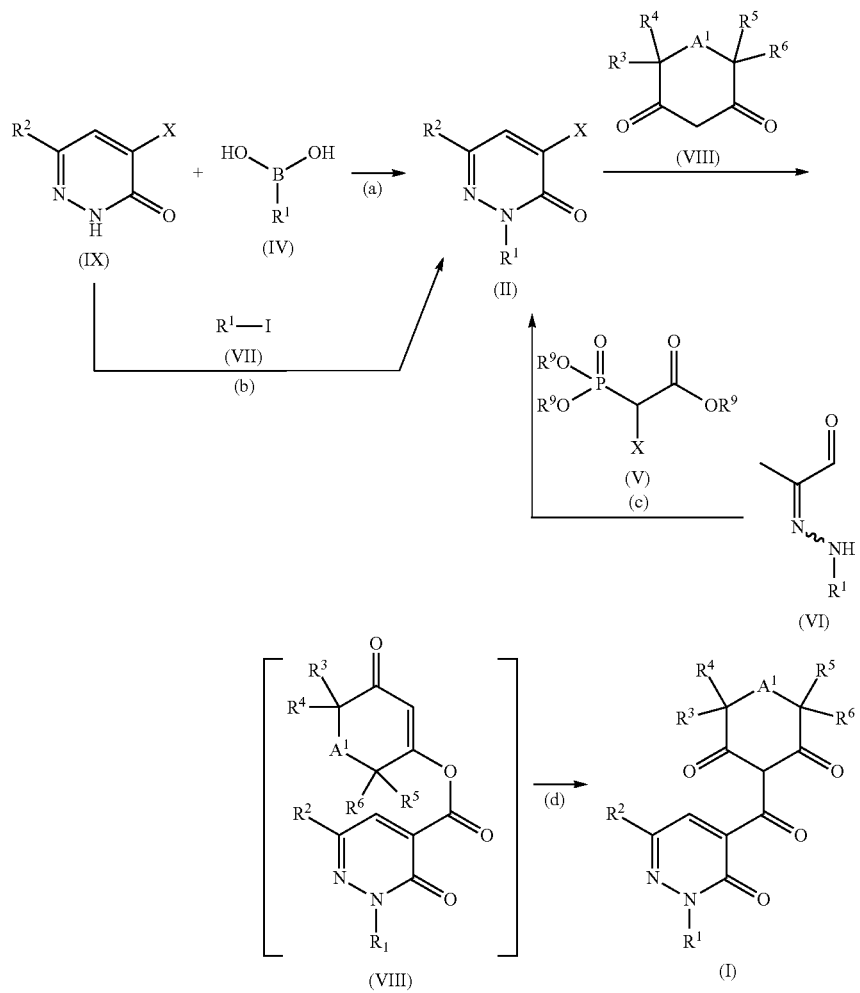

Typically small amounts of the enol ester of Formula (VIII) are continuously generated in the presence of the large effective excess of the cyclohexanedione and base.

Step (a):

Compounds of Formula (II) can be prepared by reacting a pyridazinone of Formula (IX)

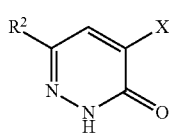

wherein $R^2$ is as defined above for the compound of Formula (I) with a boronic acid of Formula (IV)

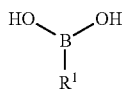

wherein $R^1$ is as defined above for the compound of Formula (I) in the presence of a base, a copper catalyst and oxygen as for example described in Monnier, F.; Tailefer, M. Topics in Organomet. Chem. 2013, 46, 173.

Suitable copper catalysts include, but are not limited to CuCl, CuBr, CuI, Cu(OAc)$_2$ and Cu$_2$O. The most preferred catalyst is Cu(OAc)$_2$.

Suitable bases include, but are not limited to alkali metal hydroxides and carbonates such as NaOH, KOH, K$_2$CO$_3$ and Na$_2$CO$_3$ as well as amine bases such as Et$_3$N, iPr$_2$NEt and pyridine. The most preferred bases are pyridine and Na$_2$CO$_3$.

The reactions between compounds of Formula (IX) and (IV) are preferably carried out in the presence of a solvent. Suitable solvents include, but are not limited to polar organic solvents such as DMF, 1,2-dichloroethane, acetonitrile, EtOAc, iPrOAc, dimethylacetamide, sulpholane and NMP. The most preferred solvents are DMF, dimethylacetamide and NMP.

The reaction can be carried out at a temperature from 25° C. to 120° C., more preferably from 40° C. to 80° C.

Preferably the reaction is run while continuously purging with an oxygen/nitrogen mixture. Concentration of oxygen can be from 5 to 100%, preferably between 5 and 25%, more preferably 22% (air).

Step (b):

Alternatively, compounds of Formula (II) can be prepared by reacting pyridazinone of formula (IX)

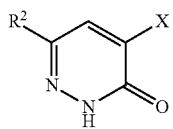

wherein $R^2$ is as defined above for the compound of Formula (I) and X is a chloro, bromo or iodo with a compound of Formula (VII)

R$^1$—I     (VII)

wherein $R^1$ is selected from the group consisting of C$_1$-C$_6$alkyl, C$_1$-C$_6$haloalkyl, C$_1$-C$_3$alkoxy, C$_1$-C$_3$alkyl-, C$_1$-C$_3$alkoxy, C$_2$-C$_3$alkoxy, C$_1$-C$_3$alkyl-, C$_1$-C$_6$haloalkyl, C$_2$-C$_6$haloalkenyl, C$_1$-C$_3$alkoxy-C$_1$-C$_3$haloalkyl in the presence of a base.

Step (c):

Alternatively, compounds of Formula (II) wherein X is chloro, $R^1$ is aryl and a 5 or 6-membered heteroaryl, wherein the heteroaryl contains one to three heteroatoms each independently selected from the group consisting of oxygen, nitrogen and sulphur, and wherein the aryl and heteroaryl component may be optionally substituted by one or more substituents selected from the group consisting of halo, C$_1$-C$_3$alkyl, C$_1$-C$_3$haloalkyl, C$_1$-C$_3$ alkoxy, cyano, acetylamino, nitro and $R^2$ is C$_1$-C$_6$ alkyl or C$_3$-C$_6$ cycloalkyl can be prepared by reacting aldehyde of Formula (VI)

wherein $R^1$ is aryl and a 5 or 6-membered heteroaryl, wherein the heteroaryl contains one to three heteroatoms each independently selected from the group consisting of oxygen, nitrogen and sulphur, and wherein the aryl and heteroaryl component may be optionally substituted by one or more substituents selected from the group consisting of halo, C$_1$-C$_3$alkyl, C$_1$-C$_3$haloalkyl, C$_1$-C$_3$ alkoxy, cyano, acetylamino, nitro with a phosphonate of Formula (V)

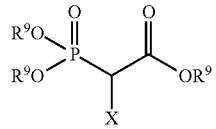

wherein X is chloro and $R^9$ is C$_1$-C$_3$alkyl in the presence of a base and an alcoholic solvent.

Suitable bases include, but are not limited to alkali metal alkoxides such as NaOEt, NaOMe, KOtBu and NaOtBu.

A suitable alcoholic solvents include, but are not limited to MeOH, EtOH, iPrOH and tBuOH.

The reaction can be carried out at a temperature from −25° C. to 40° C., preferably from 0° C. to 20° C.

Alternatively, compounds of Formula (II) wherein $R^1$ is 3,4-dimethoxyphenyl and $R^2$ is as defined in Formula (I) and X is Br can be prepared by a process which comprises reacting a compound of Formula (IX)

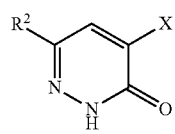

with a halogenating agent to provide a compound of Formula (X)

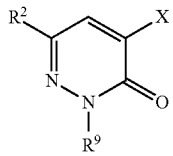

wherein X is Br and R⁹ is selected from the group consisting of Cl, Br and I, preferably Cl;

and then reacting a compound of Formula (X) with a compound of Formula (XI)

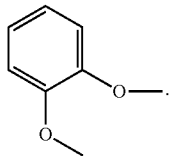

in the presence of a radical initiator and base or by irradiating the reaction mixture with visible light in the presence of a suitable sensitizer and base.

Suitable halogenating (chlorinating agents) include sodium hypochlorite, t-butyl hypochlorite and other alkyl hypochlorites, chlorine, NCS, trichloroisocyanuric acid. Sodium hypochlorite is preferred The initial reaction can be performed under homogeneous conditions (with t-butyl hypochlorite) or in a two phase system (with aq. sodium hypochlorite) and organic solvent in the presence of a neutralizing agent (acid, buffer) which is added in parallel with sodium hypochlorite solution.

Also the reaction can be simply performed in water (with sodium hypochlorite or chlorine) and the product is isolated by filtration Suitable solvents include chlorobenzene, dichloromethane, toluene and MTBE. Chlorobenzene and dichloromethane being preferred.

Suitable acidifying agents include mineral acids (e.g HCl, $H_2SO_4$), carboxylic acids (e.g AcOH), phosphate buffer, sodium bicarbonate.

The initial reaction can be carried out at a temperature from −5° C. to 80° C., preferably from 25° C. to 40° C.

Compound (X) can be isolated in pure form by crystallisation from the organic solvent used for the reaction or by simple evaporation of the organic layer. It can be also used in solution in the subsequent reaction.

With regard to the conversion of compound (X) to compound (II), suitable solvents include toluene, chlorobenzene, 1,2-dichlorobenzene, benzonitrile, TBME, acetonitile, butyronitrile, dichloromethane, 1,2-dichloroethane, ethyl acetate, isopropyl acetate. chlorobenzene is preferred.

Phase transfer catalysts can also be employed in order to improve the speed and yield of the reaction and include, for example, $Bu_4NCl$ and Aliquat 336.

Radical initiators include, but are not limited to, AIBN, benzoyl peroxide, lauroyl peroxide, bis(tert-butylcyclohexyl) peroxydicarbonate (DCHPC), tert-butyl hydroperoxide, cumene hydroperoxide (CHP), methyl ethyl ketone peroxide (MEKP), potassium peroxodisulfate. Cumene hydroperoxide (CHP) and methyl ethyl ketone peroxide (MEKP) are preferred.

It should also be noted that the Compound of Formula (IX) can be converted to a compound of Formula (II) in a single-step procedure. Thus compound (X) can be generated (and continuously consumed upon generation) in situ allowing performing the transformation of (IX) to (II) in a single step. Also, stoichiometric amount of base is not needed in this case. Typically a solution of sodium hypochlorite is added to a mixture of Compound (IX), 1,2-dimethoxybenzene, organic solvent, aqueous buffer solution, phase transfer catalyst and a radical initiator. Radical initiator can be also added simultaneously with a sodium hypochlorite solution.

Alternatively, a photochemical catalysed procedure can be employed. Suitable bases in this aspect include, but are not limited to inorganic bases such as $K_2CO_3$, $Cs_2CO_3$, $Na_2CO_3$, $NaHCO_3$, sodium acetate, potassium acetate, NaOH and phosphate buffer.

The reaction can be carried out at a temperature from 20° C. to 80° C., preferably from 30° C. to 40° C.

Alternatively, the compound of formula (II) wherein X=bromo and $R^1$=aryl (especially 3,4-dimethoxyphenyl) as defined above can be obtained from an electrolysis of pyridazinone (IX) in presence of a compound of Formula (XI) and an electrolyte in an organic solvent. This procedure has an advantage in that it is not necessary for the reaction to proceed via an intermediate of Formula (X).

The electrolysis can be performed in a batch-type reaction mode with a defined current passed through the reaction mixture by employing electrodes connected to a power supply device or by a flow-type reaction mode of flowing the reaction mixture through an electrolysis flow cell. The most preferred electrolysis reaction mode is the flow-electrolysis.

Suitable electrode materials include, but are not limited to graphite, glassy carbon, DSA, Ir/Ta MOX, Ir/Ti MOX as anode material and graphite, glassy carbon, steel, copper, platinum as cathode material. Preferred material is Ir/Ta MOX for the anode and steel (V2A) for the cathode.

Suitable electrolytes include, but are not limited to salts of type $A^+B^-$ where $A^+$=$Na^+$, $K^+$, $NR_4^+$ (with R=H or alkyl), and where $B^-$=acetate, pivalate, benzoate, fluoride. Further electrolytes include, but are not limited to organic electrolytes, namely, tetramethyl guanidine, DBU, triethyl amine, 4-N,N'-dimethylamino pyridine, HFIP, acetic acid. Preferred electrolytes are carboxylate salts sodium- and potassium pivalate.

Suitable solvents include but are not limited to alcohols MeOH, EtOH, iPrOH, tBuOH, HFIP with MeOH being the preferred solvent.

The electrolysis can be carried out at a temperature from −20° C. to 60° C., preferably from 5° C. to 35° C.

The present invention thus still further provides a compound of Formula (X)

(X)

wherein R⁹ is selected from the group consisting of Cl, Br and I, preferably Cl (i.e 4-bromo-2-chloro-6-methyl-pyridazin-3-one).

Step (d)

The compound of Formula (I) can be advantageously prepared by reacting a compound of Formula (II) with a compound of Formula (III) in the presence of a base, palladium catalyst, a suitable phosphine or phosphine salt and carbon monoxide.

Suitable bases include, but are not limited to inorganic bases such as $K_2CO_3$, $Cs_2CO_3$, $Na_2CO_3$, NaOH as well as amine bases such as triethylamine, diisopropylethylamine and DBU. The most preferred bases are triethylamine and diisopropylethylamine.

Suitable palladium catalysts include, but are not limited to $Pd(OAc)_2$, $PdCl_2$, Pd/C, $PdBr_2$, $PdCl_2(PhCN)_2$, $Pd_2dba_2$, $Pd(PPh_3)_4$ and $PdCl_2(cinnamyl)_2$. The most preferred catalyst is $Pd(OAc)_2$. The amount of palladium catalyst is from 0.0001 to 0.05 equivalents, more preferably between 0.0005 and 0.005 equivalents.

Suitable phosphines and phospine salts include, but are not limited to monodentate phosphines such as $Ph_3P$, $Cy_3P$, $nBuPAd_2$, $tBu_3P \cdot HBF_4$ and XPhos as well bidentate ligands such as Xantphos, Josiphos, Dpephos, dcpb, dcpp and BINAP. The most preferred phosphine ligands are Xantphos and Dpephos when X=Br and dcpb when X=Cl. The amount of phospine ligands is from 0.0001 to 0.05 equivalents, more preferably between 0.0005 and 0.005 equivalents.

The reaction is conducted under the atmosphere of carbon monoxide. The pressure is from 1 to 50 bar, more preferably between 2 and 10 bar.

The reactions between compound of Formula (II) and compound of Formula (III) are preferably carried out in the presence of a solvent. Suitable solvents include, but are not limited to polar aprotic solvents such as acetonitrile, anisole, dioxane, THF, EtOAc, MTBE, PrCN. The most preferred solvent is acetonitrile.

The reaction can be carried out at a temperature from 20° C. to 120° C., preferably from 40° C. to 70° C.

Various aspects and embodiments of the present invention will now be illustrated in more detail by way of the following non-limiting examples.

The following abbreviations are used: s=singlet; br s=broad singlet; d=doublet; dd=double doublet; dt=double triplet; t=triplet, tt=triple triplet, q=quartet, quin=quintuplet, sept=septet; m=multiplet; RT=retention time, MH⁺=molecular mass of the molecular cation.

¹H NMR spectra are recorded at 400 MHz unless indicated otherwise and chemical shifts are recorded in ppm.

Example 1

Preparation of 4-Bromo-2-(3,4-dimethoxyphenyl)-6-methyl-pyridazin-3-one

Example 1a

4-Bromo-2-(3,4-dimethoxyphenyl)-6-methyl-pyridazin-3-one

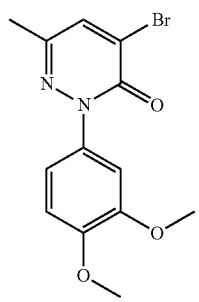

To a solution of 5-bromo-3-methyl-1H-pyridazin-6-one (5.00 g, 24.9 mmol, 94% purity) in anhydrous DMF (20 ml) was added $Cu(OAc)_2$ (1.15 g, 6.32 mmol) and pyridine (4.1 ml, 50 mmol). The resulting suspension was heated to 50° C. and a solution of 3,4-dimethoxyphenyl boronic acid (7.05 g, 37.9 mmol) in anhydrous DMF (30 ml) was added over 4.5 h via a syringe pump. During the reaction air was bubbled through the reaction mixture with vigorous stirring. The reaction was stirred for further 2 h and then cooled to ambient temperature. Dichloromethane (100 ml) was added followed by 1M HCl (200 ml). The resulting mixture was stirred for 30 min, organic layer was separated and aqueous layer extracted with dichloromethane (2×100 ml). The combined organic phase was washed with ice cold water (4×100 ml), dried over anhydrous $Na_2SO_4$ and concentrated under reduced pressure to afford crude 4-bromo-2-(3,4-dimethoxyphenyl)-6-methyl-pyridazin-3-one (10.21 g) as a brown solid. Quantitative NMR analysis using trimethoxybenzene as an internal standard indicates purity of 71% (88% yield). The crude product was suspended in TBME (50 ml) and stirred for 20 min, TBME was decanted and the same procedure was repeated two more times. After drying the residue under high vacuum afforded 4-bromo-2-(3,4-dimethoxyphenyl)-6-methyl-pyridazin-3-one (6.30 g, 95% purity, 73% isolated yield) as a light brown solid.

¹H NMR (400 MHz, CDCl₃): δ 7.58 (s, 3H), 7.16-7.12 (m, 2H), 6.95-6.92 (m, 1H), 3.92 (s, 3H), 3.90 (s, 3H), 2.39 (s, 3H).

Example 1b

Alternative Route to 4-Bromo-2-(3,4-dimethoxyphenyl)-6-methyl-pyridazin-3-one

Step 1: 4-bromo-2-chloro-6-methyl-pyridazin-3-one

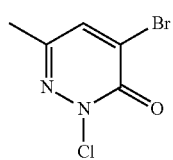

5-Bromo-3-methyl-1H-pyridazin-6-one (20.0 g, 103.8 mmol, 98.1% purity), dichloromethane (60 mL) and tert-butanol (1 mL, 10.5 mmol) were charged in a reactor. Sodium hypochlorite solution (80.3 g, 116.4 mmol, 10.8%) and glacial acetic acid (6.67 g, 116.4 mmol) were added in parallel at 23-27° C. within 40 min. The mixture was diluted with dichloromethane (150 mL) and the phases were separated. The aqueous phase was extracted with dichloromethane (60 mL). The combined organic phase was dried over anhydrous $Na_2SO_4$ and the solvent was completely removed by rotary evaporation under reduced pressure to afford a white crystalline material (23.17 g, 99% purity by quantitative NMR analysis, m.p. 145-148° C. dec.).

$^1$H NMR (400 MHz, $CDCl_3$): δ 7.54 (s, 1H), 2.35 (s, 3H).

Step 2: 4-Bromo-2-(3,4-dimethoxyphenyl)-6-methyl-pyridazin-3-one

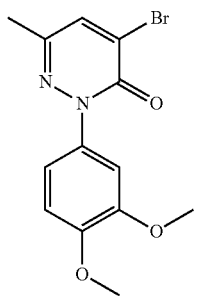

4-Bromo-2-chloro-6-methyl-pyridazin-3-one (2.00 g, 8.9 mmol, 99% purity), 1,2-dimethoxybenzene (1.48 g, 10.7 mmol), bis(4-tert-butylcyclohexyl)peroxydicarbonate (0.19 g, 0.48 mmol), sodium bicarbonate (1.13 g, 13.4 mmol), tetrabutylammonium chloride (52 mg, 0.18 mmol), chlorobenzene (20 g) and water (9 g) were charged in a flask. The mixture was heated to 60° C. for 2 h. The organic phase was separated and the aqueous phase was extracted with chlorobenezene (2×20 mL). The combined organic extract was dried over $Na_2SO_4$ and evaporated to give a brown oil (2.9 g). This material was analysed by quantitative HPLC.

Example 1c

Alternative (one-step) Route to 4-Bromo-2-(3,4-dimethoxyphenyl)-6-methyl-pyridazin-3-one 5-Bromo-3-methyl-1H-pyridazin-6-one (3.0 g, 15.0 mmol, 94.5% purity), 1,2-dimethoxybenzene (41.4 g, 300 mmol), Aliquot® 336 (0.61 g, 1.5 mmol), chlorobenzene (47 mL) and phosphate buffer solution (38 mL, 38 mmol, 1M, pH=7.2) were charged in a double jacketed reactor. A solution of sodium hypochlorite (10.6 g, 15.0 mmol, 10.6%) was added in one portion and the mixture was stirred for 10 min at RT. A solution of methyl ethyl ketone peroxide (0.99 g, 1.5 mmol, 32% in phthalate-free plasticizer mixture) in chlorobenzene (9 mL) was added simultaneously with a solution of sodium hypochlorite (58.1 g, 82.0 mmol, 10.6%) in about 3 h while keeping the temperature at 35° C. (The addition of the sodium hypochlorite solution ended up 15 min before). During this period 4 consecutive portions of 5-Bromo-3-methyl-1H-pyridazin-6-one (each portion 3.0 g, 15.0 mmol, 94.5% purity; totally 12.0 g, 65.0 mmol) were added with intervals of 40 min between each portion. The reaction mixture was stirred for 1 h at 35° C. Residual active chlorine was destroyed with a solution of sodium meta-bisulfite (5 mL, 10%). The mixture was heated to 80° C. and the aqueous lower layer was separated. The solvent and the residual amount of 1,2-dimethoxybenzene were removed by vacuum distillation. The hot product melt was diluted with 1-Butanol (73.3 g) and the resulting solution was cooled slowly to 0° C. The resulting suspension was filtered and the product was dried in a drying oven at 60° C. under vacuum.

$^1$H NMR (400 MHz, $CDCl_3$): δ 7.58 (s, 1H), 7.14-7.11 (m, 2H), 6.94-6.91 (m, 1H), 3.91 (s, 3H), 3.89 (s, 3H), 2.38 (s, 3H).

Example 1d

Alternative Route to 4-Bromo-2-(3,4-dimethoxyphenyl)-6-methyl-pyridazin-3-one

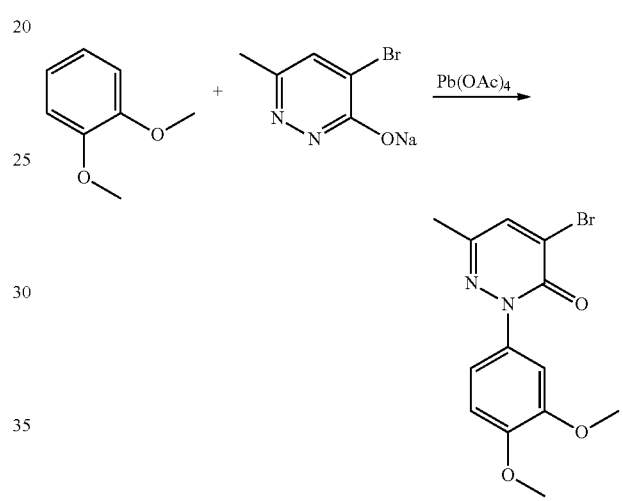

A suspension of sodium salt of 5-bromo-3-methyl-1H-pyridazin-6-one (0.177 g, 0.78 mmol), prepared beforehand by deprotonation with NaH in THF and evaporation of the reaction mixture, and $Pb(OAc)_4$ (0.437 g, 0.936 mmol) in veratrole (2.20 g, 15.6 mmol) was heated for 19 h at 100° C. The resulting brown reaction mixture was quenched by addition of aq saturated $NH_4Cl$. The mixture was then extracted with DCM, organic layer washed with water and dried over anhydrous $MgSO_4$. Evaporation under reduced pressure provided a crude product as a solution in veratrole (2.45 g).

Example 1e

Alternative Route to 4-Bromo-2-(3,4-dimethoxyphenyl)-6-methyl-pyridazin-3-one

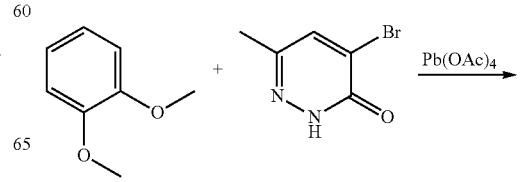

15
-continued

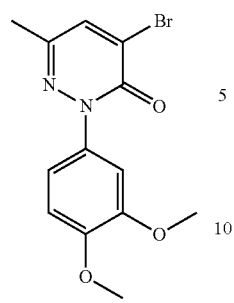

To a solution of 5-bromo-3-methyl-1H-pyridazin-6-one (1.10 g, 5.35 mmol) and veratrole (1.49 g, 10.7 mmol) in acetic acid (11 ml) was added Pb(OAc)$_4$ (3.75 g, 6.77 mmol). The resulting black suspension was stirred at 80° C. for 16 h. The reaction mixture was then cooled to ambient temperature and evaporated to near dryness under reduced pressure. The residue was diluted with DCM and poured into aq saturated NaHCO$_3$. The resulting mixture was extracted with DCM (3×), the combined organic layer was washed with brine and dried over anhydrous MgSO$_4$. Evaporation under reduced pressure provided the crude product (2.50 g).

Example 1f

Alternative Route to 4-Bromo-2-(3,4-dimethoxy-phenyl)-6-methyl-pyridazin-3-one

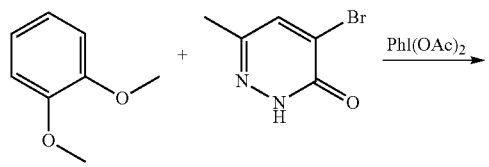

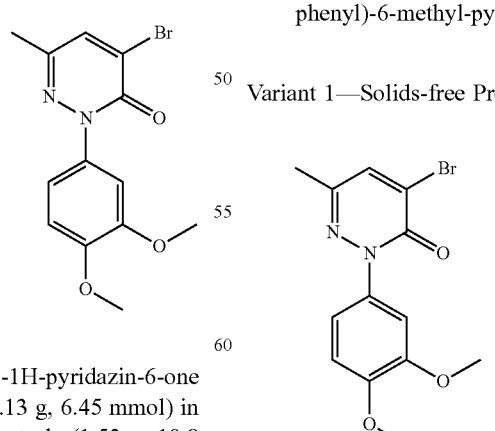

To a solution of 5-bromo-3-methyl-1H-pyridazin-6-one (1.10 g, 5.35 mmol) and PhI(OAc)$_2$ (2.13 g, 6.45 mmol) in trifluoroethanol (14 ml) was added veratrole (1.52 g, 10.8 mmol) and the resulting mixture was stirred at 70° C. for 24 h. The reaction mixture was cooled to ambient temperature and evaporated under reduced pressure.

16

Example 1g

Alternative Route to 4-Bromo-2-(3,4-dimethoxy-phenyl)-6-methyl-pyridazin-3-one

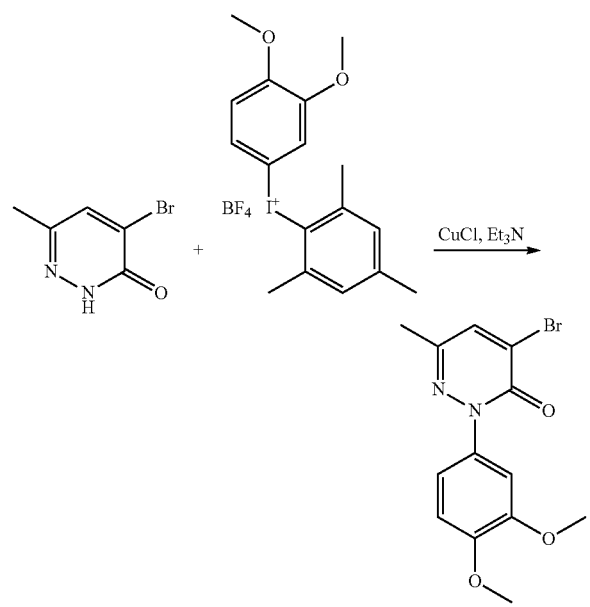

To a suspension of 5-bromo-3-methyl-1H-pyridazin-6-one (0.100 g, 0.503 mmol) and CuCl (0.0051 g, 0.050 mmol) in DCM (1.5 ml) was added triethylamine (0.11 ml, 0.75 mmol) followed by (3,4-dimethoxyphenyl)-(2,4,6-trimethylphenyl)iodonium tetrafluoroborate (0.302 g, 0.528 mmol). The resulting suspension was stirred for 14 h at ambient temperature (full conversion of starting material). The reaction mixture was diluted with DCM, washed with aq saturated NH$_4$Cl, water and brine. The organic layer was dried over anhydrous MgSO$_4$ and evaporated under reduced pressure to afford the crude product (0.279 g).

Example 1h

Alternative Route to 4-Bromo-2-(3,4-dimethoxy-phenyl)-6-methyl-pyridazin-3-one-photochemical process Variant 1—Solids-free Process 4-Bromo-2-chloro-6-methyl-pyridazin-3-one (5.0 g, 15.0 mmol, 94.5% purity), 1,2-dimethoxybenzene (5.7 g, 42 mmol), water (5.3 g 30 mmol) Ruthenium(bipyridine)dichloride.hydrate (26 mg, 0.03 mmol), acetonitrile (21 g, 511 mmol) and potassium acetate (5.8, 60 mmol) were charged in a reactor. The mixture was irradiated in the range of 420-460 nm (Blue Tuna Kessil Lamp light source) for 2 hours at room temperature with agitation. The aqueous phases was removed through extraction. The solvent and the residual amount of 1,2-dimethoxybenzene were removed by vacuum distillation.

$^1$H NMR (400 MHz, CDCl$_3$): δ 7.58 (s, 1H), 7.14-7.11 (m, 2H), 6.94-6.91 (m, 1H), 3.91 (s, 3H), 3.89 (s, 3H), 2.38 (s, 3H).

Variant 2—Suspension Process

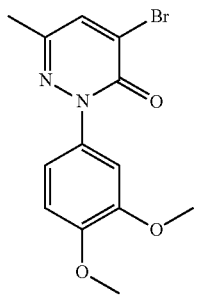

4-Bromo-2-chloro-6-methyl-pyridazin-3-one (5.0 g, 15.0 mmol, 94.5% purity), 1,2-dimethoxybenzene (5.7 g, 42 mmol), Ruthenium(bipyridine)dichloride.hydrate (26 mg, 0.03 mmol), acetonitrile (21 g, 511 mmol) and potassium acetate (5.8, 60 mmol) were charged in a reactor. The mixture was irradiated in the range of 420-460 nm (Blue Tuna Kessil Lamp light source) for 2 hours at room temperature with agitation. The aqueous phases was removed through extraction. The solvent and the residual amount of 1,2-dimethoxybenzene were removed by vacuum distillation.

$^1$H NMR (400 MHz, CDCl$_3$): δ 7.58 (s, 1H), 7.14-7.11 (m, 2H), 6.94-6.91 (m, 1H), 3.91 (s, 3H), 3.89 (s, 3H), 2.38 (s, 3H).

Example 1i

Alternative Route to 4-Bromo-2-(3,4-dimethoxyphenyl)-6-methyl-pyridazin-3-one-electrochemical process

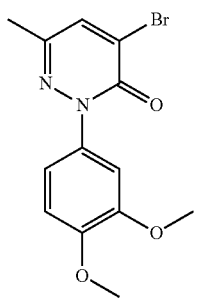

A solution of 5-bromo-3-methyl-1H-pyridazin-6-one (2.89 g, 15.0 mmol, 98% purity), veratrol (50.2 g, 360 mmol, 99% purity), potassium pivalate (2.21 g, 15.0 mmol, 95% purity) in methanol (104 g, 3.26 mol, >99% purity) was pumped (500 mL/min) through a electrolysis flow reactor (undivided, electrode surface: 80 cm$^2$, Ir/Ta MOX-anode, stainless steel-cathode, electrode-electrode distance=1 mm) at a current density of 12.5 mA/cm$^2$. The mixture was circulated through the set-up consisting of a storage tank, pump and electrolysis reactor until full conversion of starting material was obtained after 3 h.

The same general procedure as outlined in Example 1a above was used for the synthesis of compounds listed below.

Example 2

4-Bromo-2-(4-methoxyphenyl)-6-methyl-pyridazin-3-one

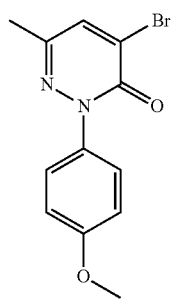 [SMILES: COc1ccc(-n2nc(C)cc(Br)c2=O)cc1]

Crude 4-bromo-2-(4-methoxyphenyl)-6-methyl-pyridazin-3-one (2.17 g) was obtained as a pale brown solid. Quantitative NMR analysis using trimethoxybenzene as an internal standard indicated purity of 61% (88% chemical yield). The crude material was purified by silica gel chromatography (0-70% EtOAc in cyclohexane) to provide 4-bromo-2-(4-methoxyphenyl)-6-methyl-pyridazin-3-one (1.10 g, 75%, 98% purity) as a white crystalline solid.

$^1$H NMR (400 MHz, CDCl$_3$): δ 7.57 (s, 1H), 7.54-7.47 (m, 2H), 7.09 (s, 1H), 7.00-6.94 (m, 2H), 3.85 (s, 3H), 2.39 (s, 3H).

Example 3

4-Bromo-6-methyl-2-[4-(trifluoromethyl) phenyl] pyridazin-3-one

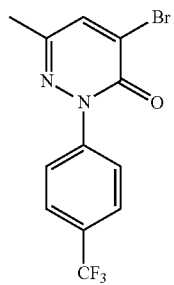 [SMILES: Cc1cc(Br)c(=O)n(-c2ccc(C(F)(F)F)cc2)n1]

Crude 4-bromo-6-methyl-2-[4-(trifluoromethyl)phenyl] pyridazin-3-one (2.17 g) was obtained as a pale beige solid. Quantitative NMR analysis using trimethoxybenzene as an internal standard indicated purity of 59% (79% chemical yield). The crude material was purified by silica gel chromatography (15-55% EtOAc in cyclohexane) to provide 4-bromo-6-methyl-2-[4-(trifluoromethyl) phenyl]pyridazin-3-one (1.25 g, 77%, >99% purity) as a white crystalline solid.

¹H NMR (400 MHz, CDCl₃): δ 7.80 (d, J=8.4 Hz, 2H), 7.74 (d, J=8.8 Hz, 2H), 7.61 (s, 1H), 2.41 (d, J=1.5 Hz, 3H).

Example 4

4-(5-Bromo-3-methyl-6-oxo-pyridazin-1-yl)benzonitrile

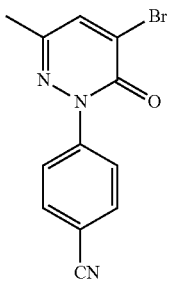 [SMILES: Cc1cc(Br)c(=O)n(-c2ccc(C#N)cc2)n1]

Crude 4-(5-bromo-3-methyl-6-oxo-pyridazin-1-yl)benzonitrile (4.56 g) was obtained as a white solid. Quantitative NMR analysis using trimethoxybenzene as an internal standard indicated purity of 33% (67% chemical yield). The crude material was purified by silica gel chromatography (20-100% EtOAc in cyclohexane) to provide 4-(5-bromo-3-methyl-6-oxo-pyridazin-1-yl)benzonitrile (1.56 g, 60%, 86% purity) as a white crystalline solid.

¹H NMR (400 MHz, CDCl₃): δ 7.88-7.74 (m, 4H), 7.61 (s, 1H), 2.42 (s, 3H).

Example 5

4-Bromo-6-methyl-2-(p-tolyl)pyridazin-3-one

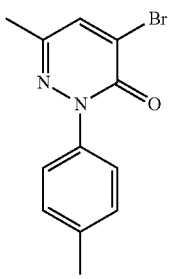 [SMILES: Cc1ccc(-n2nc(C)cc(Br)c2=O)cc1]

Crude 4-bromo-6-methyl-2-(p-tolyl)pyridazin-3-one (1.56 g) was obtained as a yellow solid. Quantitative NMR analysis using trimethoxybenzene as an internal standard indicated purity of 78% (84% chemical yield). The crude material was purified by silica gel chromatography (0-50% EtOAc in cyclohexane) to provide 4-bromo-6-methyl-2-(p-tolyl)pyridazin-3-one (1.1 g, 74%, 97% purity) as a white crystalline solid.

¹H NMR (400 MHz, CDCl₃): δ 7.58 (s, 1H), 7.46 (d, J=8.4 Hz, 2H), 7.31-7.22(m, 2H), 2.40 (s, 3H), 2.39 (s, 3H).

Example 6

4-Bromo-6-methyl-2-(m-tolyl)pyridazin-3-one

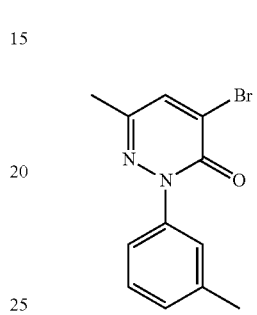

Crude 4-bromo-6-methyl-2-(m-tolyl)pyridazin-3-one (1.96 g) was obtained as a yellow solid. Quantitative NMR analysis using trimethoxybenzene as an internal standard indicated purity of 67% (90% chemical yield). The crude material was purified by silica gel chromatography (20-50% EtOAc in cyclohexane) to provide 4-bromo-6-methyl-2-(m-tolyl)pyridazin-3-one (1.22 g, 81%, 97% purity) as a white crystalline solid.

¹H NMR (400 MHz, CDCl₃): δ 7.59 (s, 1H), 7.41-7.32 (m, 3H), 7.25-7.18 (m, 1H), 2.41 (s, 3H), 2.39 (s, 3H).

Example 7

4-Bromo-6-methyl-2-(o-tolyl)pyridazin-3-one

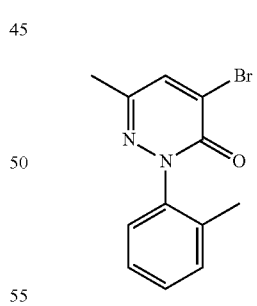

Crude 4-bromo-6-methyl-2-(o-tolyl)pyridazin-3-one (3.94 g) was obtained as a yellow oil. Quantitative NMR analysis using trimethoxybenzene as an internal standard indicated purity of 33% (59% chemical yield). The crude material was purified by silica gel chromatography (5-60% EtOAc in cyclohexane) to provide 4-bromo-6-methyl-2-(o-tolyl) pyridazin-3-one (1.34 g, 56%, 91% purity) as a yellow crystalline solid.

¹H NMR (400 MHz, CDCl₃): δ 7.63 (s, 1H), 7.38-7.29 (m, 3H), 7.26-7.23 (m, 1H), 2.39 (s, 3H), 2.17 (s, 3H).

Example 8

N-[4-(5-Bromo-3-methyl-6-oxo-pyridazin-1-yl)phenyl]acetamide

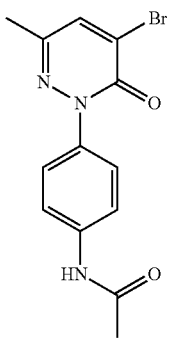 [SMILES: CC(=O)Nc1ccc(-n2nc(C)cc(Br)c2=O)cc1]

Crude N-[4-(5-bromo-3-methyl-6-oxo-pyridazin-1-yl)phenyl]acetamide (1.52 g) was obtained as a yellow solid. Quantitative NMR analysis using trimethoxybenzene as an internal standard indicated purity of 67% (61% chemical yield). The crude material was purified by silica gel chromatography (50-100% EtOAc in cyclohexane) to provide N4-[4-(5-bromo-3-methyl-6-oxo-pyridazin-1-yl)phenyl]acetamide (0.725 g, 40%, 91% purity) as a yellow crystalline solid.

$^1$H NMR (400 MHz, CDCl$_3$): δ 7.60 (s, 1H), 7.57 (d, J=8.8 Hz, 2H), 7.51 (d, J=8.8 Hz, 2H), 2.40 (s, 3H), 2.19 (s, 3H).

Example 9

4-Bromo-2,6-dimethyl-pyridazin-3-one

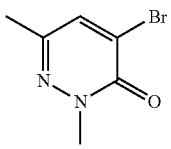

Sodium hydride in paraffin oil (60%, 0.255 g, 6.66 mmol) was added to a solution of 5-bromo-3-methyl-1H-pyridazin-6-one (1.03 g, 5.12 mmo) in DMF (7.2 mL) at 0° C. After stirring for 20 min iodomethane (6.66 mmol, 0.417 mL) was added via syringe at rt. The reaction media heated up noticeably and became dark violet. After stirring for 1 h the reaction was quenched by pouring into a mixture of aqueous NaHCO$_3$ and Na$_2$S$_2$O$_3$. The mixture was extracted with EtOAc (2×) and combined organic layer washed with water and brine. Drying over anhydrous Na$_2$SO$_4$ and evaporation under reduced pressure afforded 1.228 g of crude material as a black solid. Purification via silica gel chromatography (0-70% EtOAc in cyclohexane) provided 4-bromo-2,6-dimethyl-pyridazin-3-one (0.736 g, 70.4%, >99.5% purity) as a white solid.

$^1$H NMR (400 MHz, CDCl$_3$): δ 7.51 (s, 1H), 3.8 (s, 3H), 2.32 (s, 3H).

Example 10

4-Bromo-2-butyl-6-methyl-pyridazin-3-one

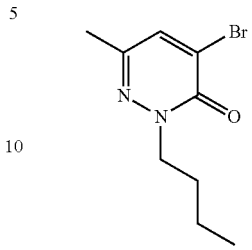

4-Bromo-2-butyl-6-methyl-pyridazin-3-one was prepared by an analogous procedure as the one described in example 9 from 1-iodobutane as a light yellow oil (1.387 g, 93.7%, 99% purity)

$^1$H NMR (400 MHz, CDCl$_3$): δ 7.48 (s, 1H), 4.19-4.12 (m, 2H), 2.32 (s, 3H), 1.84-1.73 (m, 2H), 1.44-1.33 (m, 2H), 0.96 (t, J=7.3, 3H).

Example 11

(2Z)-2-[(3,4-Dimethoxyphenyl)hydrazono]propanal

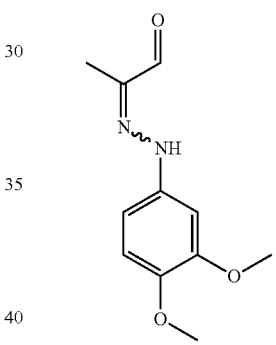

A 5 l double jacketed reactor was charged with water (1.2 l) and cooled to 5° C. Concentrated sulfuric acid (104 ml, 1.90 mol) was added slowly while keeping the temperature below 25° C. When the internal temperature had again reached 5° C. 3,4-dimethoxyaniline (198.0 g, 1.27 mol) was added portionwise. A solution of sodium nitrite (88.3 g, 1.27 mol) in water (0.25 l) was added to the dark violet suspension over 40 min while keeping the internal temperature below 5° C. The reaction mixture was stirred at 0° C. for 90 min followed by addition of the solution of 3-dimethylamino-2-methyl-2-propanal (137.2 g, 1.15 mol) and NaOAc (105.0 g, 1.27 mol) in water (0.75 l) over 1 h while keeping the internal temperature below 5° C. After the addition was finished the reaction mixture was gradually allowed to reach 20° C. over 2.5h The resulting black suspension was transferred into 5 l Erlenmeyer flask and the reactor was washed with water (2 l) to remove most of the remaining precipitate. The solid product was filtered off, washed on filter with water (1.5 l) and dried to constant weight at 50° C. and high vacuum for 40 h to yield (2Z)-2-[(3,4-dimethoxyphenyl)hydrazono]propanal (199 g, 92% purity, 71% yield) as a red solid. This material was sufficiently pure to be used in the next step.

Upon standing for 16 h at room temperature another portion of the product precipitated out from the aqueous phase and was also filtered, washed and dried in vacuum to provide the second crop of (2Z)-2-[(3,4-dimethoxyphenyl)hydrazono]propanal (43.7 g, 70% purity, 12% yield; 83% yield for combined both batches).
¹H NMR (400 MHz, CDCl₃): δ 9.49 (s, 1H), 8.10 (br s, 1H), 7.00 (d, J=2.6 Hz, 1H), 6.86 (d, J=8.4 Hz, 1H), 6.70 (dd, J=8.6, 2.4 Hz, 1H), 3.94 (s, 3H), 3.88 (s, 3H), 1.98 (s, 3H).

Example 12

4-Chloro-2-(3,4-dimethoxyphenyl)-6-methyl-pyridazin-3-one

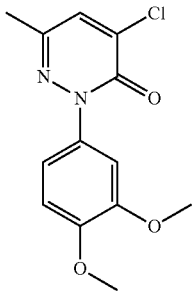

(2Z)-2-[(3,4-dimethoxyphenyl)hydrazono]propanal (4.80 g, 96% purity, 20.7 mmol) was suspended in EtOH (62 ml). Triethyl 2-chloro-2-phosphonoacetate (6.57 g, 24.9 mmol) was added at 0° C. followed by NaOEt (2.20 g, 31.1 mmol). The reaction was stirred at 0° C. for 45 min before another portion of NaOEt (2.20 g, 31.1 mmol) was added. After stirring for further 45 min the reaction was quenched by addition of aq saturated NaHCO₃. The resulting mixture was extracted by DCM (3×), combined organic layers were washed with brine, dried over anhydrous Na₂SO₄ and concentrated under reduced pressure. The obtained residue was suspended in Et₂O, stirred for 30 min and the precipitate was filtered off and dried to afford 4-chloro-2-(3,4-dimethoxyphenyl)-6-methyl-pyridazin-3-one (4.91 g, 98% purity, 82% yield) as a fair brown solid.
¹H NMR (400 MHz, CDCl₃): δ 7.34 (s, 3H), 7.16-7.12 (m, 2H), 6.95-6.91 (m, 1H), 3.91 (s, 3H), 3.89 (s, 3H), 2.38 (s, 3H)

Example 13

2-[2-(3,4-Dimethoxyphenyl)-6-methyl-3-oxo-pyridazine-4-carbonyl]cyclohexane-1,3-dione

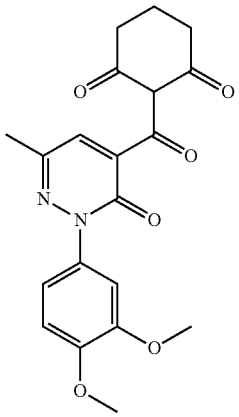 [SMILES: COc1ccc(-n2nc(C)cc(C(=O)C3C(=O)CCCC3=O)c2=O)cc1OC]

Method A

A pressure reactor (100 mL) was charged with 4-bromo-2-(3,4-dimethoxyphenyl)-6-methyl-pyridazin-3-one (3.00 g, 8.9 mmol), freshly purified 1,3-cyclohexadione (1.31 g, 11.6 mmol), palladium acetate (0.00204 g, 0.00890 mmol) and Dpephos (0.00489 g, 0.0890 mmol). The system was flushed with argon, and then triethylamine (2.51 mL, 17.8 mmol) and acetonitrile (12.5 mL) were added. The reaction mixture was stirred under 10 bar of CO at 60° C. for 4 h. After flushing with Ar and cooling to ambient temperature the reaction mixture was concentrated under reduced pressure. The residue was picked up in DCM (100 mL) and washed with 1M HCl (75 mL). Aq. phase was extracted with DCM (2×100 ml). Combined organic layers were dried over Na₂SO₄, filtered and evaporated to afford crude 2-[2(3,4-dimethoxyphenyl)-6-methyl-3-oxo-pyridazine-4-carbonyl]cyclohexane-1,3-dione (3.858 g) of yellow-brown foam. Quantitative NMR analysis using trimethoxybenzene as a standard indicated purity of 81.7% (chemical yield 92%). This material was suspended in EtOH (7.5 ml), heated to reflux and stirred for 30 min yielding a clear solution. After cooling to ambient temperature the resulting precipitate was filtered off, washed on filter with a small amount of Et₂O and dried under high vacuum to afford 2-[2-(3,4-dimethoxyphenyl)-6-methyl-3-oxo-pyridazine-4-carbonyl]cyclohexane-1,3-dione (2.819 g, 99.2% purity, 82% isolated yield) as a bright yellow solid.
¹H NMR (400 MHz, CDCl₃): δ 16.15 (s, 1H), 7.15-7.11 (m, 1H), 7.10-7.08 (m, 2H), 6.91 (d, J=8.4 Hz, 1H), 3.90 (s, 3H), 3.89 (s, 3H), 2.72 (t, J=6.2 Hz, 2H), 2.48-2.43 (m, 2H), 2.41 (s, 3H), 2.04 (quin, J=6.4 Hz, 2H).

Method B

A pressure vial was charged with 4-bromo-2-(3,4-dimethoxyphenyl)-6-methyl-pyridazin-3-one (0.200 g, 0.603 mmol), 1,3-cyclohexanedione (0.102 g, 0.905 mmol), Pd(OAc)₂ (0.00276 g, 0.0121 mmol) and bis(1-adamantyl)-butyl-phosphane (0.00606 g, 0.0169 mmol). The system was flushed with argon, then diisopropylethyl amine (0.21 ml, 1.21 mmol) and acetonitrile (2.5 ml) were added. The reaction mixture was stirred under 10 bar of CO at 80° C. for 18 h. After cooling to ambient temperature and flushing with argon the reaction mixture was filtered through a pad of celite. The filtrate was concentrated under reduced pressure, residue was dissolved in dichloromethane and washed with aq saturated NH₄Cl. The aqueous phase was extracted with dichloromethane (2×), the combined organic layers were dried over anhydrous Na₂SO₄ and concentrated under reduced pressure to yield 2-[2-(3,4-dimethoxyphenyl)-6-methyl-3-oxo-pyridazine-4-carbonyl]cyclohexane-1,3-dione (0.2684 g) as a yellow foam. Quantitative NMR analysis using trimethoxybenzene as an internal standard indicated purity of 57.8% (67% chemical yield)

Method C

A pressure vial was charged with 4-chloro-2-(3,4-dimethoxyphenyl)-6-methyl-pyridazin-3-one (0.200 g, 0.698 mmol), 1,3-cyclohexanedione (0.103 g, 0.91 mmol), Pd(OAc)₂ (0.0032 g, 0.014 mmol) and 1,4-bis(dicyclohexylphosphino)-butane (0.0064 g, 0.014 mmol). The system was flushed with argon, then triethylamine (0.20 ml, 1.4 mmol) and acetonitrile (2.5 ml) were added. The reaction mixture was stirred under 10 bar of CO at 80° C. for 18 h. After cooling to ambient temperature and flushing with argon the reaction mixture was filtered through a pad of celite. The filtrate was concentrated under reduced pressure, residue was dissolved in dichloromethane and washed with aq saturated NH₄Cl. The aqueous phase was extracted with dichloromethane (2×), the combined organic layers were dried over anhydrous Na₂SO₄ and concentrated under reduced pressure to yield 2-[2-(3,4-dimethoxyphenyl)-6-methyl-3-oxo-pyridazine-4-carbonyl]cyclohexane-1,3-dione (0.295 g) as a brown foam. Quantitative NMR analysis using trimethoxybenzene as an internal standard indicated purity of 49% (54% chemical yield)

The following compounds were prepared using Method A:

Example 14

2-[2-(4-Methoxyphenyl)-6-methyl-3-oxo-pyridazine-4-carbonyl]cyclohexane-1,3-dione

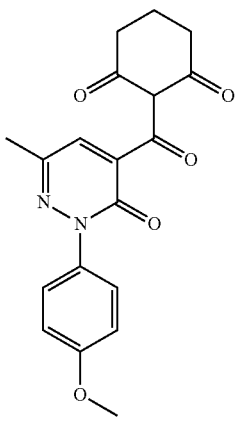 [SMILES: COc1ccc(-n2nc(C)cc(C(=O)C3C(=O)CCCC3=O)c2=O)cc1]

Crude 2-[2-(4-methoxyphenyl)-6-methyl-3-oxo-pyridazine-4-carbonyl]cyclohexane-1,3-dione (0.541 g) was obtained as a yellow foam. Quantitative NMR analysis using trimethoxybenzene as an internal standard indicated purity of 82% (95% chemical yield).
¹H NMR (400 MHz, CDCl₃): δ 16.14 (br s, 1H), 7.54-7.46 (m, 2H), 7.09 (s, 1H), 6.99-6.93 (m, 2H), 3.83 (s, 3H), 2.73 (t, J=6.2 Hz, 2H), 2.47 (t, J=5.9 Hz, 2H), 2.41 (s, 3H), 2.10-1.99 (m, 2H).

Example 15

2-[6-Methyl-3-oxo-2-carbonyl]cyclohexane-1,3-dione

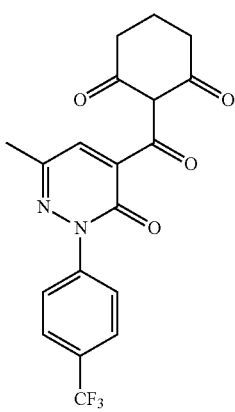 [SMILES: Cc1cc(C(=O)C2C(=O)CCCC2=O)c(=O)n(-c2ccc(C(F)(F)F)cc2)n1]

Crude 2-[6-methyl-3-oxo-2-[4-(trifluoromethyl)phenyl]pyridazine-4-carbonyl]cyclohexane-1,3-dione (0.531 g) was obtained as an orange foam. Quantitative NMR analysis using trimethoxybenzene as an internal standard indicated purity of 76% (86% chemical yield).
¹H NMR (400 MHz, CDCl₃): δ 16.15 (s, 1H), 7.79 (d, J=8.4 Hz, 2H), 7.71 (d, J=8.8 Hz, 2H), 7.10 (s, 1H), 2.75 (t, J=6.4 Hz, 2H), 2.48 (t, J=6.6 Hz, 2H), 2.43 (s, 3H), 2.10-2.03 (m, 2H).

Example 16

4-[5-(2,6-Dioxocyclohexanecarbonyl)-3-methyl-6-oxo-pyridazin-1-yl]benzonitrile

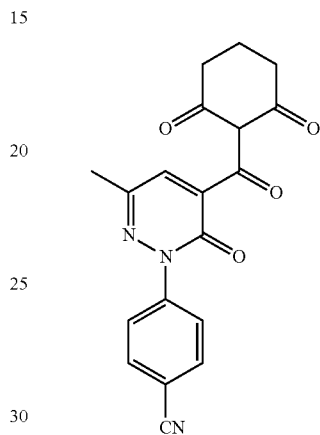

Crude 4-[5-(2,6-dioxocyclohexanecarbonyl)-3-methyl-6-oxo-pyridazin-1-yl]benzonitrile (0.482 g) was obtained as a yellow foam. Quantitative NMR analysis using trimethoxybenzene as an internal standard indicated purity of 50% (58% chemical yield).
¹H NMR (400 MHz, CDCl₃): δ 16.16 (s, 1H), 7.85-7.82 (m, 2H), 7.76-7.72 (m, 2H), 7.08 (s, 1H), 2.76 (t, J=6.2 Hz, 2H), 2.49 (m, 2H), 2.43 (s, 3H), 2.11-2.03 (m, 2H).

Example 17: 2-[6-Methyl-3-oxo-2-(p-tolyl)pyridazine-4-carbonyl]cyclohexane-1,3-dione

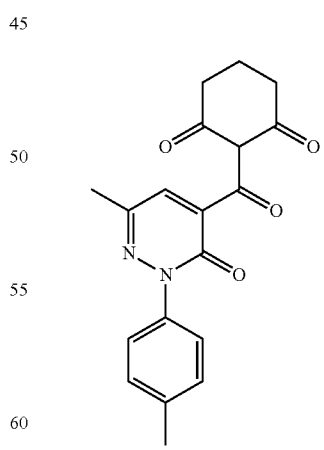

Crude 2-[6-methyl-3-oxo-2-(p-tolyl)pyridazine-4-carbonyl]cyclohexane-1,3-dione (0.531 g) was obtained as a green foam. Quantitative NMR analysis using trimethoxybenzene as an internal standard indicated purity of 81% (92% chemical yield).

¹H NMR (400 MHz, CDCl₃): δ 16.13 (s, 1H), 7.47-7.43 (m, 2H), 7.25 (d, J=8.1 Hz, 2H), 7.10 (s, 1H), 2.73 (t, J=6.4 Hz, 2H), 2.47 (t, J=6.4 Hz, 2H), 2.41 (s, 3H), 2.38 (s, 3H), 2.09-2.01 (m, 2H).

Example 18

2-[6-Methyl-3-oxo-2-(m-tolyl)pyridazine-4-carbonyl]cyclohexane-1,3-dione

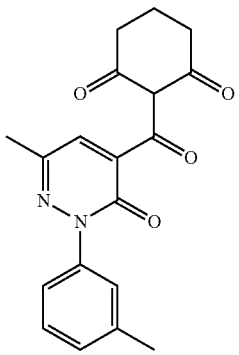 [SMILES: Cc1cccc(-n2nc(C)cc(C(=O)C3C(=O)CCCC3=O)c2=O)c1]

Crude 2-[6-methyl-3-oxo-2-(m-tolyl)pyridazine-4-carbonyl]cyclo hexane-1,3-dione (0.528 g) was obtained as a yellow foam. Quantitative NMR analysis using trimethoxybenzene as an internal standard indicated purity of 83% (94% chemical yield).
¹H NMR (400 MHz, CDCl₃): δ 16.14 (s, 1H), 7.39-7.31 (m, 2H), 7.18 (d, J=6.6 Hz, 2H), 7.10 (s, 1H), 2.73 (t, J=6.4 Hz, 2H), 2.48 (t, J=6.4 Hz, 2H), 2.42 (s, 3H), 2.40 (s, 3H), 2.10-2.01 (m, 2H).

Example 19

2-[6-Methyl-3-oxo-2-(o-tolyl)pyridazine-4-carbonyl]cyclohexane-1,3-dione

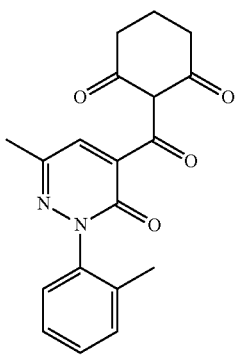 [SMILES: Cc1cc(C(=O)C2C(=O)CCCC2=O)c(=O)n(-c2ccccc2C)n1]

Crude 2-[6-methyl-3-oxo-2-(o-tolyl)pyridazine-4-carbonyl] cyclo hexane-1,3-dione (0.525 g) was obtained as a yellow foam. Quantitative NMR analysis using trimethoxybenzene as an internal standard indicated purity of 80% (95% chemical yield).
¹H NMR (400 MHz, CDCl₃): δ 16.03 (br s, 1H), 7.34-7.24 (m, 4H), 7.17 (s, 1H), 2.71 (t, J=6.2 Hz, 2H), 2.46 (t, J=6.2 Hz, 2H), 2.41 (s, 3H), 2.23 (s, 3H), 2.08-1.99 (m, 2H).

Example 20

N-[4-[5-(2,6-Dioxocyclohexanecarbonyl)-3-methyl-6-oxo-pyridazin-1-yl]phenyl]acetamide

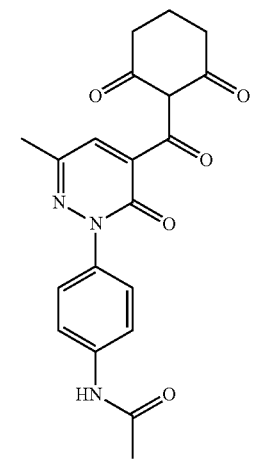 [SMILES: CC(=O)Nc1ccc(-n2nc(C)cc(C(=O)C3C(=O)CCCC3=O)c2=O)cc1]

Crude N-[4-[5-(2,6-dioxocyclohexanecarbonyl)-3-methyl-6-oxo-pyridazin-1-yl]phenyl]acetamide (0.545 g) was obtained as a yellow foam. Quantitative NMR analysis using trimethoxybenzene as an internal standard indicated purity of 65% (83% chemical yield).
¹H NMR (400 MHz, CDCl₃): δ 16.19 (br s, 1H), 7.59-7.47 (m, 4H), 7.09 (s, 1H), 2.74 (t, J=6.2 Hz, 2H), 2.47 (t, J=6.6 Hz, 2H), 2.41 (s, 3H), 2.14 (s, 3H), 2.09-2.01 (m, 2H).

Example 21

2-(2,6-Dimethyl-3-oxo-pyridazine-4-carbonyl)cyclohexane-1,3-dione

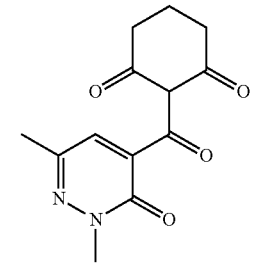 [SMILES: Cc1cc(C(=O)C2C(=O)CCCC2=O)c(=O)n(C)n1]

Crude 2-(2,6-dimethyl-3-oxo-pyridazine-4-carbonyl)cyclohexane-1,3-dione (0.586 g) was obtained as a yellow gum. Quantitative NMR analysis using trimethoxybenzene as an internal standard indicated purity of 78% (89% chemical yield).
¹H NMR (400 MHz, CDCl₃): δ 16.16 (s, 1H), 7.04 (s, 1H), 3.74 (s, 1H), 2.75 (t, J=6.2 Hz, 2H), 2.49 (t, J=6.6 Hz, 2H), 2.35 (s, 3H), 2.11-2.03 (m, 2H).

Example 22

2-(2-Butyl-6-methyl-3-oxo-pyridazine-4-carbonyl)cyclohexane-1,3-dione

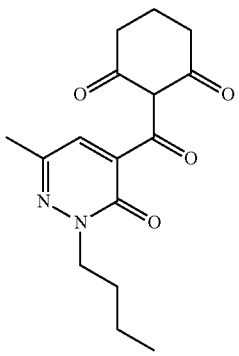 [SMILES: CCCCn1nc(C)cc(C(=O)C2C(=O)CCCC2=O)c1=O]

Crude 2-(2-butyl-6-methyl-3-oxo-pyridazine-4-carbonyl)cyclohexane-1,3-dione (0.559 g) was obtained as a yellow gum. Quantitative NMR analysis using trimethoxybenzene as an internal standard indicated purity of 73% (83% chemical yield).

$^1$H NMR (400 MHz, CDCl$_3$): δ 16.16 (s, 1H), 7.01 (s, 1H), 4.10 (t, J=7.3, 2H), 2.73 (t, J=6.2, 2H), 2.48 (t, J=6.6 Hz, 2H), 2.35 (s, 3H), 2.11-2.02 (m, 2H), 1.81-1.71 (m, 2H), 1.44-1.32 (m, 2H), 0.94 (t, J=7.3 Hz, 3H).

Example 23

2-(3-Methyl-6-oxo-1H-pyridazine-5-carbonyl)cyclohexane-1,3-dione

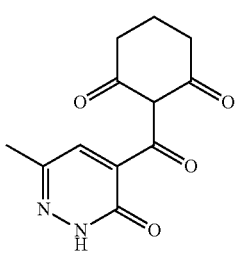 [SMILES: Cc1cc(C(=O)C2C(=O)CCCC2=O)c(=O)[nH]n1]

Crude 2-(3-methyl-6-oxo-1H-pyridazine-5-carbonyl)cyclohexane-1,3-dione (1.480 g) was obtained as a beige foam. Quantitative NMR analysis using trimethoxybenzene as an internal standard indicated purity of 65% (79% chemical yield).

$^1$H NMR (400 MHz, CDCl$_3$): δ 16.10 (br s, 1H), 11.44 (br s, 1H), 7.09 (s, 1H), 2.80-2.69 (m, 2H), 2.55-2.45 (m, 2H), 2.35 (s, 3H), 2.12-2.03 (m, 2H).

What is claimed is:

1. A process for producing a compound of Formula (I):

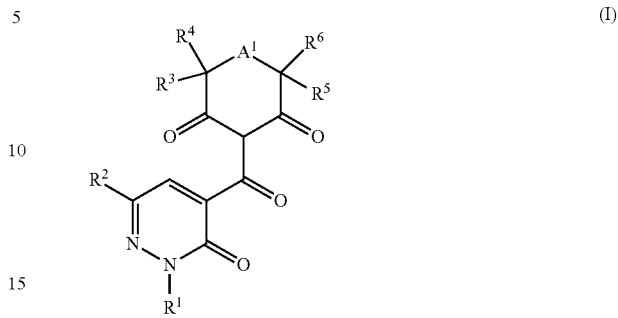

wherein
R$^1$ is selected from the group consisting of hydrogen, C$_1$-C$_6$alkyl, C$_1$-C$_6$haloalkyl, C$_1$-C$_3$alkoxyC$_1$-C$_3$alkyl-, C$_1$-C$_3$alkoxyC$_2$-C$_3$alkoxyC$_1$-C$_3$alkyl-, aryl and a 5 or 6-membered heteroaryl, wherein the heteroaryl contains one to three heteroatoms each independently selected from the group consisting of oxygen, nitrogen and sulphur, and wherein the aryl and heteroaryl component may be optionally substituted;
R$^2$ is C$_1$-C$_6$ alkyl or C$_3$-C$_6$ cycloalkyl;
A$^1$ is selected from the group consisting of O, C(O) and (CR$^7$R$^8$); and
R$^4$, R$^6$, R$^7$ and R$^8$ are each independently selected from the group consisting of hydrogen and C$_1$-C$_4$alkyl;
R$^3$ and R$^5$ are each independently selected from the group consisting of hydrogen and C$_1$-C$_4$alkyl or together may form a C$_1$-C$_3$alkylene chain;
the process comprising reacting a compound of Formula (II)

wherein X is a halogen;
with a compound of Formula (III)

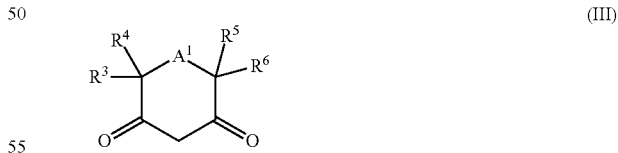

wherein A$^1$ and R$^3$, R$^4$, R$^5$ and R$^6$ are as defined with regard to Formula (I) above;
in a reaction medium comprising:
(i) a palladium catalyst;
(ii) a suitable phosphine ligand or phosphine ligand salt;
(iii) a suitable base; and
(iv) carbon monoxide;
to give a compound of Formula (I).

2. A process according to claim 1, wherein R$^1$ is an optionally substituted heteroaryl.

3. A process according to claim 1, wherein $R^1$ is an optionally substituted phenyl.

4. A process according to claim 3, wherein $R^1$ is phenyl optionally substituted by one or more substituents selected from the group consisting of halo, $C_1$-$C_4$alkyl, $C_1$-$C_4$haloalkyl, $C_1$-$C_3$ alkoxy, cyano and nitro.

5. A process according to claim 4, wherein $R^1$ is 3,4-dimethoxyphenyl.

6. A process according to claim 1, wherein $R^2$ is methyl.

7. A process according to claim 1, wherein X is selected from the group consisting of Br, Cl and I.

8. A process according to claim 1, wherein X is Br.

9. A process according to claim 1, wherein $A^1$ is $CR^7R^8$ and $R^3$, $R^4$, $R^5$, $R^6$, $R^7$ and $R^8$ are hydrogen.

10. A process according to claim 1, wherein the reaction medium further comprises (v) a solvent.

11. A process according to claim 10, wherein the solvent is acetonitrile.

12. A compound of Formula (IIa1a)

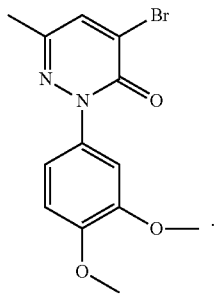

(IIa1a)

13. A process for producing a compound of Formula (IIa1a), comprising reacting a compound of Formula (X)

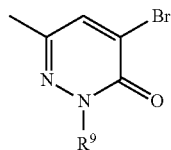

(X)

wherein $R^9$ is selected from the group consisting of Cl, Br and I;
with a compound of Formula (XI)

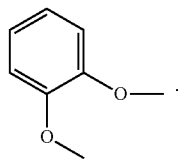

(XI)

14. A process according to claim 13, wherein Compound (X) and Compound (XI) are reacted using a photochemical catalysed procedure.

15. A compound of Formula (X)

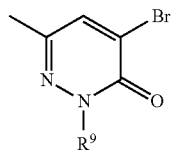

(X)

wherein $R^9$ is selected from the group consisting of Cl, Br and I.

* * * * *